United States Patent
Kurth et al.

(10) Patent No.: US 8,048,061 B2
(45) Date of Patent: Nov. 1, 2011

(54) TAPERED FITTING FOR AN INTRODUCER COUPLED TO A HEMOSTATIC VALVE

(75) Inventors: Paul A. Kurth, Rancho Palos Verdes, CA (US); Andrew W. Armour, Media, PA (US); Joseph J. Thomas, Malvern, PA (US); Douglas A. Kratz, Chester Springs, PA (US)

(73) Assignee: Pressure Products Medical Supplies, Inc., Santa Barbara, CA (US)

( * ) Notice: Subject to any disclaimer, the term of this patent is extended or adjusted under 35 U.S.C. 154(b) by 768 days.

(21) Appl. No.: 10/277,476

(22) Filed: Oct. 22, 2002

(65) Prior Publication Data

US 2004/0024381 A1 Feb. 5, 2004

Related U.S. Application Data

(60) Provisional application No. 60/400,004, filed on Jul. 31, 2002.

(51) Int. Cl.
*A61M 25/16* (2006.01)
(52) U.S. Cl. .................................................... 604/533
(58) Field of Classification Search ............. 604/104, 604/158, 169, 200–202, 205, 236–238, 272, 604/527, 534, 535, 531, 539, 284, 164.11, 604/164.05, 164.01–164.07, 165.01, 165.03, 604/166.01, 171, 264, 525, 523, 524, 256, 604/537, 246, 247, 249, 164.1, 160–161, 604/526, 167.01–167.06, 533–536; 606/108
See application file for complete search history.

(56) References Cited

U.S. PATENT DOCUMENTS

| | | | | |
|---|---|---|---|---|
| 4,645,494 A * | 2/1987 | Lee et al. | ...................... | 604/175 |
| 5,125,904 A * | 6/1992 | Lee | ................................ | 604/256 |
| 5,250,033 A * | 10/1993 | Evans et al. | ..................... | 604/160 |
| 5,376,077 A * | 12/1994 | Gomringer | .............. | 604/167.06 |
| 5,441,504 A * | 8/1995 | Pohndorf et al. | .............. | 606/129 |
| 5,520,665 A * | 5/1996 | Fleetwood | ..................... | 604/537 |
| 6,159,198 A * | 12/2000 | Gardeski et al. | .............. | 604/523 |
| 6,331,176 B1 * | 12/2001 | Becker et al. | ................. | 604/533 |
| 6,692,462 B2 * | 2/2004 | Mackenzie et al. | ........... | 604/104 |
| 6,712,791 B2 * | 3/2004 | Lui et al. | ................... | 604/167.04 |
| 2001/0049499 A1 * | 12/2001 | Lui et al. | .................. | 604/164.05 |

FOREIGN PATENT DOCUMENTS

| WO | WO 95/13840 | * | 5/1995 |
|---|---|---|---|
| WO | WO 9513840 A1 | * | 5/1995 |
| WO | WO 9906099 A2 | * | 2/1999 |

* cited by examiner

*Primary Examiner* — Theodore Stigell
(74) *Attorney, Agent, or Firm* — Daniel L. Dawes; Marcus C. Dawes

(57) ABSTRACT

An adapter for an introducer comprises a medical device having a tubular port on a proximal end such as a splittable hemostatic valve. A tubular fitting is provided on a proximal end of the introducer. An elastomeric member is disposed between the port of the medical device and the tubular fitting of the introducer for providing a fluid tight and mechanically secure connection therebetween. The introducer and valve are manually connectable and reconnectable with each other while maintaining the fluid tight connection between them. A side port may communicate with the hemostatic valve, the side port having a controllable valve ending. In the preferred embodiment the introducer comprises a splittable introducer. In the illustrated embodiment the elastomeric member provides a slip fit between the medical device and the tubular fitting of the introducer. A tab extends from the tubular fitting of the introducer to facilitate manual manipulation of the tubular fitting. In the preferred embodiment, the introducer is torqueable and the tab is used to rotate the introducer.

37 Claims, 3 Drawing Sheets

`US 8,048,061 B2`

TAPERED FITTING FOR AN INTRODUCER COUPLED TO A HEMOSTATIC VALVE

RELATED APPLICATIONS

This application is related to U.S. Provisional Patent Application, Ser. No. 60/400,004, filed Jul. 31, 2002, which is incorporated herein by reference and to which priority is claimed pursuant to 35 USC 119.

BACKGROUND OF THE INVENTION

1. Field of the Invention

The invention relates to the field of endovascular introducers used in combination with hemostatic valves, catheters and medical instruments of any kind.

2. Description of the Prior Art

Introducers are generally used with indwelling catheters and electrode leads and more particularly to introduce catheters and electrode leads into a desired portion of a patient's body. Catheters and leads are typically placed in a desired location in a patient's body, particularly within the patient's vasculature, by means of introducer systems. These introducer systems typically include an elongated sheath which is inserted into the blood vessel, artery or other portion of the patient's body, through which sheath the catheter or lead is introduced. In those circumstances in which the lead or catheter is to remain in the patient's body for a considerable period of time, it is desirable to be able to remove the introducer sheath over connectors or fittings on the leads or catheters, which may have diameters greater than the inner diameter of the introducer sheath. In many circumstances, it is also desirable that a hemostasis valve be provided at the proximal end of the introducer sheath, allowing the introducer to be sealed around the lead or catheter body. The presence of the hemostasis valve, which typically includes a rigid housing containing a compressible seal, which engages the circumference of the lead body, can pose a problem with regard to removal of the introducer sheath. In some introducers, the introducer sheath is provided with a luer hub on its proximal end, allowing interconnection both to the removable hemostasis valve and to other devices such as valves, T-fittings and the like, using the luer hub.

While allowing a variety of devices to be fitted to the introducer, the limitation exists that all such devices must be provided with a luer connector. While luer connectors are well known they are not compatible with all devices.

What is needed is some kind of connector for an introducer that is widely universal in its design compatibility and which is inexpensive and simple to manufacture.

BRIEF SUMMARY OF THE INVENTION

The invention is an adapter for an introducer comprising a medical device having a port on a distal end and a fitting provided on a proximal end of the introducer The port and fitting may have any mutually conforming shape desired, such as a tubular, conical or mutually conforming straight or tapered prismatic shape of any cross-section, such as round, square, rectangular, star shaped, oval, or helical. The introducer and medical device are manually connectable and reconnectable with each other while maintaining the fluid tight connection between them. The collar can be coated with a lubricant such as silicone fluid or any other medical grade lubricant that facilitates the insertion and removal of the collar into the mating fitting.

In one embodiment, an elastomeric member is disposed between the port of the medical device and the tubular fitting of the introducer for providing a fluid tight and mechanically secure connection therebetween. The elastomeric member may be inserted in, on or around the port of the medical device or the fitting. Thus, the fitting may provide either a male or female type connection to the medical device with or without the elastomeric member and if with the elastomeric member, then with the elastomeric member combined either with the medical device or with the fitting or with neither. The elastomeric member may be fixed to a distal end of the port of the medical device, to the tubular fitting, or may be a separate piece alternatively slip fit either into the distal end of the port of the medical device or into tubular fitting.

In the illustrated embodiment the medical device comprises a hemostatic valve, which preferably is a splittable hemostatic valve, but also expressly includes nonsplittable valves within the scope of the invention. A side port may communicate with the hemostatic valve, the side port having a controllable valve ending. In the preferred embodiment the introducer comprises a slittable introducer.

In one embodiment the elastomeric member is separable and is comprised of a resilient material with a durometer between 20 shore A and 100 shore A. More particularly, the elastomeric member is comprised of silicone rubber and has a line of fissure defined therein or is pre-slit. In the preferred embodiment, the elastomeric member has a lubricated surface. For the purposes of this specification, "separable" is defined to mean that the object so described can be split open, cut open, torn open, cracked open, popped open, snapped open, opened on a hinge or otherwise physically configured to allow the removal from the object of an elongate member, wire or catheter which is disposed through the object.

In the illustrated embodiment the elastomeric member provides a slip fit between the medical device and the tubular fitting of the introducer. The slip fit allows for a quick, simple, repeatable and reliable connection and reconnection action between the introducer and medical device with a minimum of construction complexity and expense. A tab extends from the tubular fitting of the introducer to facilitate manual manipulation of the tubular fitting. In the preferred embodiment, the introducer is reinforced with braid so that it is torqueable and the tab is used to rotate the introducer.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
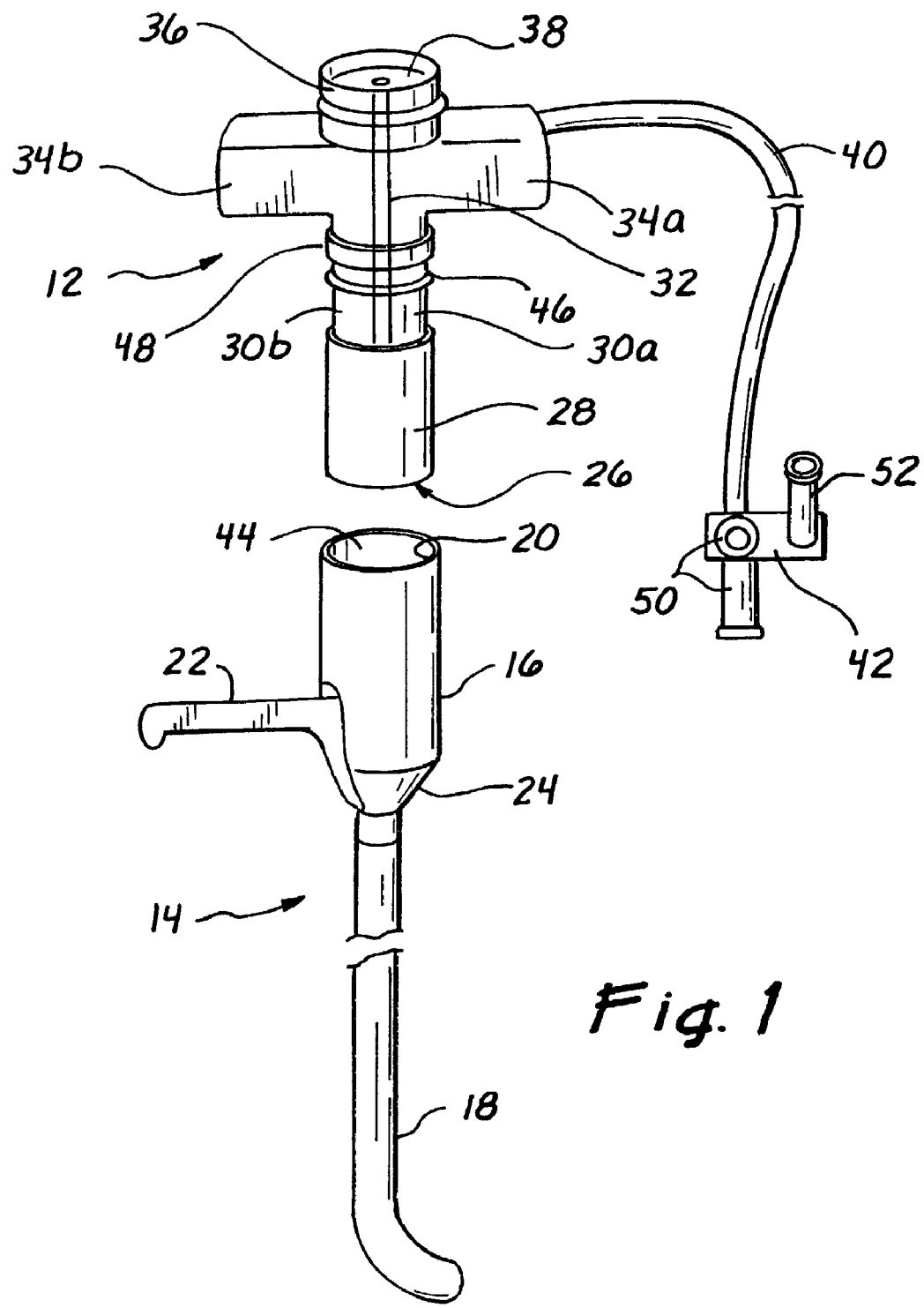
FIG. 1 is a side elevational view of the invention showing a splittable valve separated from or unengaged from the introducer.

As shown in side elevational view of FIG. 1 a cardiac or endovascular apparatus 10 is shown in the illustrated embodiment as comprised of a splittable and preferably, a rigid hemostatic valve 12 with an introducer 14. Introducer 14 is comprised of an elongated hollow tubular member 18, which is coupled with tapered fitting 16 on its proximal end. Any type of introducer 14 now known or later devised may be used in the claimed combination of the invention. For example, introducer may be reinforced or unreinforced so that it is torqueable or torsionally flexible. Introducer 14 may be splittable, slittable, tearable or separable by some means or may be integral and inseparable. Introducer 14 may be straight, curved, biased, unbiased, moldable, unmoldable or characterized variations in length, diameter, stiffness, resiliency, softness, hardness or composition along its longitudinal extent. In other words, introducer 14 should be understood in the present specification to be generally inclusive of all and any type of introducer structure or characterization.

Tapered fitting 16 is comprised of a thin walled cylindrical hollow proximal portion 20, which tapers down through a funnel-shaped portion 24 to connect with or integrally extend into or with tubular member 18.

In the illustrated embodiment, tapered fitting 16 includes a molded tab 22 extending from its lower portion in a generally perpendicular direction. Tab 22 is firmly connected to fitting 16 and provides a convenient means for manually holding, pushing, pulling, and turning fitting 16. Tapered fitting 16 slip fits or is snugly telescopically disposed in a fluid tight sealing relationship with distal end 26 of valve 12. Distal end or portion 26 of valve 12 is provided with an elastomeric collar 28 which serves to enhance the slip fit with fitting 16 and provide the fluid tight seal. Elastomeric collar 28 may be composed of any material now known or later devised to provide quick, fluid tight engagement with the interior walls of fitting 16, such as silicone rubber or any rubberized plastic or polymer. Collar 28 can be coated with a lubricant such as silicone fluid or any other medical grade lubricant that facilitates the insertion and removal of collar 28 into a mating fitting, such as tapered fitting 16.

Except for its modification at its distal end 26, valve 12 is conventional and may also include any type of hemostatic valve now known or later devised. In the illustrated embodiment a splittable or slittable valve 12 is employed which is molded or formed from two valve halves 30a and 30b. Valve 12 is held or manipulated by means of a pair of opposing upper tabs 34a and 34b extending at right angles to the axis of longitudinal symmetry of valve 12. Tabs 34a and 34b can be used to snap or tear valve 12 apart. While valve 12 is shown as splittable, it is to be expressly understood that valves comprised of separate halves, which are resiliently opened or closed like a clam shell, are also contemplated. Alternative constructions, such a valves which open against a resilient spring mechanism, are cut apart, break apart on weakened seams, or any other means for separating or opening the body of the valve are deemed to be equivalent to the illustrated embodiment. The proximal portion of valve 12 is provided with a conventional splittable or separable hub 36 having an elastomeric sealing membrane 38 therein. Again hub 36 may be provided with any type of design desired or needed to connect with other medical devices or tubing.

In the illustrated embodiment, fitting 16 has a smooth interior bore or surface 44 with which collar 28 makes intimate contact. The outer diameter of collar 28 and the inner diameter of fitting 16 are such that given the elasticity of both collar 28 and fitting 16, a tight sealing fit is achieved through which not only is a fluid tight seal made, but valve 12 and introducer 14 are mechanically coupled together with sufficient strength so that they will not easily be disconnected from each other by the forces encountered in normal handling. However, their coupling is not so strong, that the physician has any substantial difficulty in either making or disconnecting the coupling between valve 12 and introducer 14. Hence, collar 28 of valve 12 and fitting 16 of introducer 14 may be coupled and uncoupled multiple times without losing the ability to make a fluid tight and mechanically secure connection.

Figure 2:
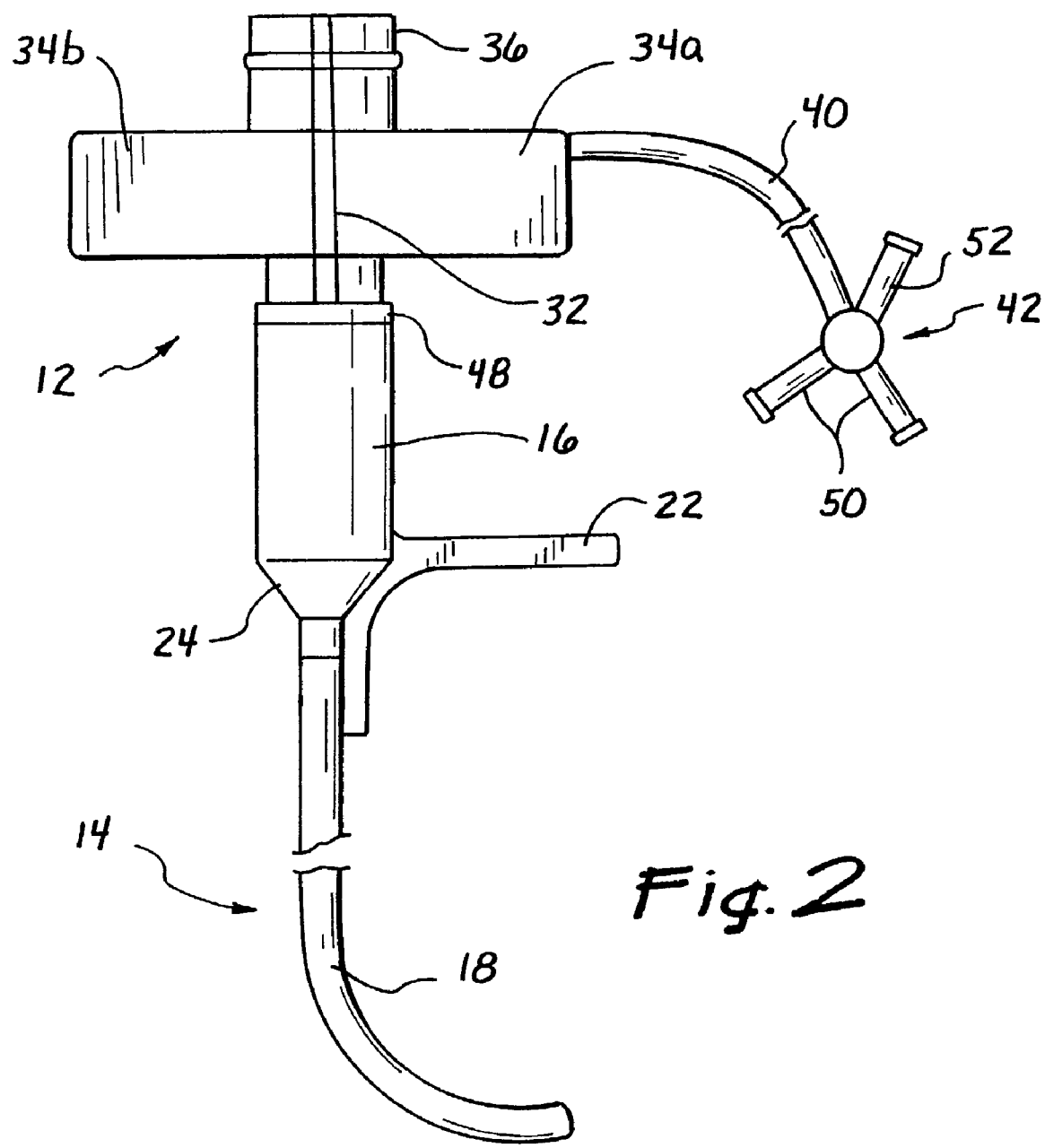
FIG. 2 is a side elevational view of the invention showing the embodiment of FIG. 1 with the splittable valve inserted into or engaged with the introducer.

FIG. 2 is a side elevational view of the invention which illustrates apparatus 10 in an assembled configuration. Collar 28 is telescopically forced or Inserted into fitting 16 deeply enough to cause circular circumferential hard ridge 46 on valve halves 30a and 30b to be inserted into the upper portion of fitting 16 to provide a compression fit. Collar 28 is illustrated in FIGS. 1 and 2 as fixed to the distal end or port of valve 12, but it is entirely within the scope of the invention that collar 28 may be fixed within proximal portion 20 of fitting 16, or may be a free piece which is alternatively slip fit either on distal end or port of valve 12 or into proximal portion 20 of fitting 16 according to user choice.

Fitting 16 can be forced further up valve halves 30a and 30b until its upper proximal edge 20 comes into contact with a circular circumferential hard stop 48. This serves to limit the degree of insertion and to avoid overstressing fitting 16, which has a slight inner tapering or cone shape.

While the illustrated embodiment is shown as being coupled together by slip fit elastic members, it is also to be understood that similar couplings using Luer lock structures or other positive screw or locking structures can be added or combined with the disclosed fitting/collar combination. In other words, the coupling of a cylindrical or slightly conical elastomeric plug into a cylindrical or slightly conical hollow tube end may be further modified to include additional structure such as locking structures, threading, rings, keyways, guides, collars and any other type of connection mechanism.

The inner chamber within valve 12 may be communicated with a side port 40, which terminates in a conventional three-way valve 42. Valve 42 communicates with tubular ports 50 for connection to external tubing and is operated by manually turning a cylinder valve element (not shown) by means of a lever 52. This allows the infusion of fluids into valve 12 and ultimately introducer 14. Further details of the design of valve 42 is immaterial to the scope of the invention.

Thus, it can now be readily appreciated that introducer 14 with fitting 16 is provided with an adapter which allows introducer 14 to be quickly and securely connected to multiple alternative medical devices according to the medical application at hand. For example, in the simplest embodiment introducer 14 may be combined with a splittable valve 12 and a pacemaker lead implanted into a patient through valve 12 and introducer 14. In such a procedure, valve 12 would normally be broken open after the pacemaker lead was implanted. After implantation if for any reason it should be desired to remove the first pacemaker lead and replace it with a second lead, then a new valve 12 can be inserted into introducer 14, which might be left in place, and the procedure repeated. In prior art embodiments where the valve and introducer were integral, such a replacement procedure would require subcutaneous reinsertion of the introducer with the attendant risk of additional tissue trauma and complication.

Figure 3:
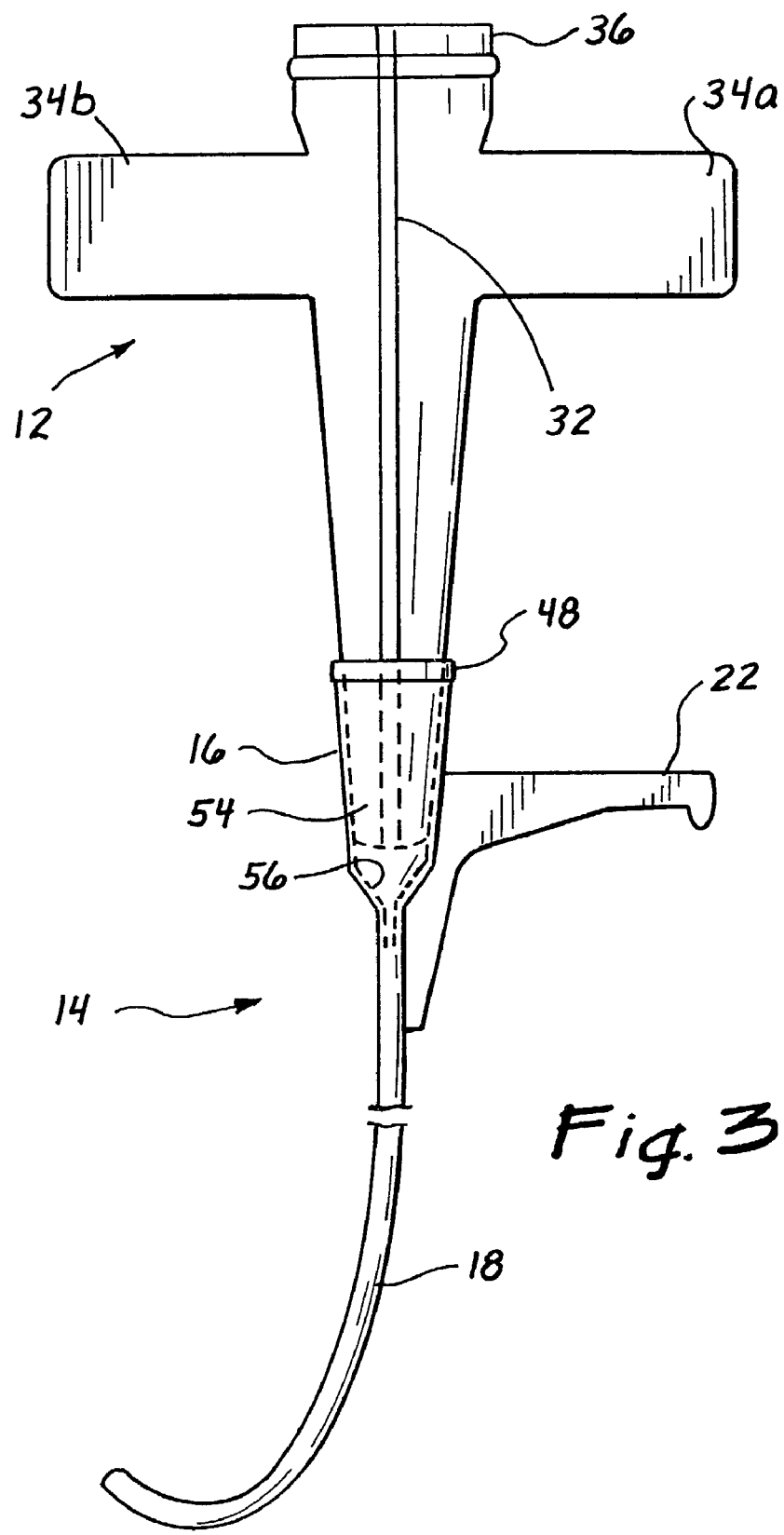
FIG. 3 is a side elevational view of the invention showing an embodiment where a medical device or valve without a side port is directly slip fit into the proximal fitting of the introducer without any sealing elastomeric member.

FIG. 3 is a simplified side elevational view of another embodiment where valve 12 is connected to introducer 14 by a slip fit of a hard plastic distal port 54 that wedges into the proximal end of a hard plastic fitting 16. The distal port 54 is shown as generally tubular or conical and as slip fitting into a conforming tubular or conical bore 56 defined in the proximal end of a hard plastic fitting 16 without the mediation of any elastomeric gasket or seal between them. It is within the scope of the invention that the relationship may be reversed, i.e. the proximal end of a hard plastic fitting 16 may be formed as a male-type tubular or conical port which inserts into a female-type tubular or conical port of valve 12.

The medical device may be any type hemostatic valve now know or later devised. While splittable and nonsplittable valves have been described above, the invention expressly contemplates being used as an adapter for translatable or slideable valves which are moved or rotated in and out of an operative position, such as shown in U.S. Pat. No. 5,441,504 or PCT Publication WO 02/05867, both of which are incorporated herein by reference.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A separable medical adapter for use with an introducer with a tubular fitting provided on a proximal end of the introducer, the adapter comprising:

a separable hemostatic valve arranged and configured to be separable along a line of fissure or weakened seam into at least two portions with a separable body arranged and configured to be separable along a line of fissure or weakened seam into at least two portions having a distal end; and at least one fixed, compressible, and torqueable separable elastomeric member arranged and configured to be separable along a line of fissure or weakened seam into at least two portions and capable of being concentrically disposed on the distal end of the separable body, supported and compressed between the separable body of the hemostatic valve and the tubular fitting of the introducer when the separable body of the hemostatic valve and tubular fitting are compression fit together, the distal end of the body of the separable hemostatic valve and the tubular fitting being composed of firmer material than the separable elastomeric member, the elastic composition of the separable elastomeric member being such that it is sufficiently compressed between the separable body of the hemostatic valve and the tubular fitting to provide a mechanically secure, but hemostatic, reconnectable and torqueable connection therebetween by means of a compression seal and friction of the body of the separable hemostatic valve and tubular fitting with the separable elastomeric member, so that introducer can be equally torqued in either direction through the medical adapter.

2. The separable adapter of claim 1 where the elastomeric member is fixed to the distal end of the body.

3. The separable adapter of claim 1 where the elastomeric member is fixed to the tubular fitting.

4. The separable adapter of claim 1 where the elastomeric member is a separate piece alternatively compression fit either on the distal end of the port of the body or into the tubular fitting.

5. The separable adapter of claim 1 where the tubular fitting further comprises a tab extending therefrom to facilitate manual manipulation of the tubular fitting.

6. The separable adapter of claim 1 where the elastomeric member is comprised of a resilient material with a durometer between 20 shore A and 100 shore A.

7. The separable adapter of claim 1 where the elastomeric member is pre-slit.

8. The separable medical adapter of claim 1 where the elastomeric member is comprised of silicone rubber.

9. The separable medical adapter of claim 1 further comprising a side port communicated with the hemostatic valve.

10. The separable medical adapter of claim 1 further comprising at least one tab fixed to the body of the hemostatic valve to manipulate the body.

11. A separable medical adapter for use with an introducer, the adapter comprising:
   a separable hemostatic valve arranged and configured to be separable along a line of fissure or weakened seam into at least two portions with a separable body arranged and configured to be separable along a line of fissure or weakened seam into at least two portions having a distal end and at least one tab fixed to the body to serve as a means for manually holding a portion of the body as the body is opened and to manipulate the body; and
   at least one separable, fixed, compressible and torqueable elastomeric member arranged and configured to be separable along a line of fissure or weakened seam into at least two portions capable of being concentrically disposed around a distal portion of the separable body of the hemostatic valve for providing a mechanically secure connection between the separable body of the separable hemostatic valve and introducer when the separable body of the separable hemostatic valve and introducer are coupled together, the separable elastomeric member being confined by the introducer and supported by the separable body of the separable hemostatic valve to provide a reconnectable and torqueable hemostatic seal between the separable body of the separable hemostatic valve and the introducer by means of the compression of the separable elastomeric member and friction between the separable body of the separable hemostatic valve and introducer with the separable elastomeric member, so that introducer can be equally torqued in either direction through the medical adapter.

12. The separable adapter of claim 11 where the elastomeric member is bonded to the body and separates when the body is opened.

13. The separable introducer of claim 11 further comprising a fitting provided on a proximal end of the introducer and at least one tab fixed to the fitting to serve as a means for manually holding the introducer as the introducer is separated into separate pieces.

14. The separable medical adapter of claim 11 further comprising a side port communicated with the hemostatic valve.

15. A combination of a medical sealing adapter and an introducer having a fitting on its proximal end, the adapter comprising:
   a hemostatic valve with a separable body arranged and configured to be, separable along a line of fissure or weakened seam into at least two portions having a distal end; and
   at least one fixed, compressible and torqueable elastomeric member which is capable of being disposed around the distal end of the body of the hemostatic valve to hemostatically seal and mechanically secure the distal end of the body of the hemostatic valve and the fitting together, the distal end of the body of the hemostatic valve and the fitting composed of a firmer material than the elastomeric member, the elastomeric member being radially supported and circumferentially compressed between the distal end of the body of the hemostatic valve and the fitting to provide a concentric compression seal when the fitting and distal end of the body of the hemostatic valve are telescopically coupled together, the body of the hemostatic valve and fitting sandwiching the softer elastomeric member between them and an elastic composition of the elastic member having a softness selected to provide a reconnectable and torqueable coupling between the body of the hemostatic valve and the fitting by means of the compression of the elastomeric member and the friction of the fitting with the elastomeric member, so that introducer can be equally torqued in either direction through the medical adapter.

16. The combination of claim 15 where the body and the fitting are reconnectable with each other multiple times without any substantial loss of ability to provide the compression seal.

17. The combination of claim 15 where the body and the introducer are rotatable as a unit when the body and the introducer are connected together when the introducer is implanted.

18. The combination of claim 15 further comprising a side port communicated with the hemostatic valve.

19. The combination of claim 15 where elastomeric member is fixed to the port of the body.

20. The combination of claim 15 where the elastomeric member is fixed to the fitting.

21. The combination of claim 15 where the elastomeric member is a separate piece alternatively compression fit either on the distal end of body or into the fitting.

22. The combination of claim 15 where the distal end of the medical sealing adapter and introducer are compression fit together to provide the hemostatic seal.

23. The combination of claim 15 where the elastomeric member provides a compression fit between the body and the fitting of the introducer.

24. The combination of claim 15 where the fitting further comprises a tab extending therefrom to facilitate manual manipulation of the fitting.

25. A separable medical adapter for use with an introducer, the adapter comprising:
   a separable hemostatic valve arranged and configured to be separable along a line of fissure or weakened seam into at least two portions with a separable body arranged and configured to be separable along a line of fissure or weakened seam into at least two portions and having tabs extending from the body adapted for manipulation of the hemostatic valve; and
   a fixed, compressible and torqueable separable elastomeric member arranged and configured to be separable along a line of fissure or weakened seam into at least two portions concentrically disposed around a portion of the separable body for providing a hemostatic seal and mechanically secure connection with the introducer, the separable body being defined as torqueable due to a compression fit of the elastomeric member between the body of the hemostatic valve and tubular fitting of the introducer sufficient to provide the mechanically secure connection between the hemostatic valve body and tubular fitting, which mechanically secure connection allows torque to be securely transmitted to the introducer from the hemostatic valve body, the separable elastomeric member which is supported and confined between the introducer and the separable body of the separable hemostatic valve and having the elastic composition providing the hemostatic seal and allowing for torquing of the introducer by manipulating the adapter body by means of the compression of the separable elastomeric member of the hemostatic valve body and the friction of the tubular fitting of the introducer with the separable elastomeric member, the distal end of the separable body of the separable hemostatic valve and the fitting being composed of firmer material than the separable elastomeric member.

26. The separable medical adapter of claim 25 where the separable-body is sliceable, splittable, or peelable along at least one score line or along at least one line of fissure or weakened seam.

27. The separable medical adapter of claim 25 further comprising a side port communicated with the hemostatic valve.

28. The separable medical adapter of claim 25 where the introducer is separable.

29. A separable medical adapter for use with an introducer, the adapter comprising:
 a hemostatic valve with a body having a distal portion; and
 a separable, fixed, compressible and torqueable elastomeric member concentrically disposed around the distal portion of the body of the hemostatic valve for providing a hemostatic seal and mechanically secure connection between the introducer and the body of the hemostatic valve, the separable elastomeric member being defined as torqueable due to a compression fit of the elastomeric member between the body of the hemostatic valve and tubular fitting of the introducer sufficient to provide a mechanically secure connection between the hemostatic valve body and tubular fitting, which mechanically secure connection allows torque to be securely transmitted to the introducer from the hemostatic valve, the amount of elastomeric member which is supported and concentrically confined between the introducer and the body of the hemostatic valve and the elastic composition being such that a hemostatic seal is provided and torquing of the introducer is allowed by manipulating the adapter by means of the compression of the elastomeric member and the friction of the elastomeric member between the body of the hemostatic valve and the introducer.

30. The separable medical adapter of claim 29 further comprising a side port communicated with the hemostatic valve.

31. A medical apparatus comprising:
 an introducer;
 a hemostatic valve with a body having a distal portion; and
 a separable, fixed, compressible and torqueable elastomeric member concentrically disposed around the distal portion of the body of the hemostatic valve for providing a hemostatic seal and mechanically secure connection of the body of the hemostatic valve with the introducer when confined between the body of the hemostatic valve and introducer by means of the compression of and the friction with the body of the hemostatic valve and introducer, the separable elastomeric member being defined as torqueable due to a compression fit of the elastomeric member between the body of the hemostatic valve and tubular fitting of the introducer sufficient to provide a mechanically secure connection between the hemostatic valve body and tubular fitting, which mechanically secure connection allows torque to be securely transmitted to the introducer from hemostatic valve, the hemostatic seal and mechanically secure connection provided by the amount of the elastomer member confined between the body of the hemostatic valve and introducer fitting and provided by the nature of the elastic composition of the elastomeric member.

32. The medical apparatus of claim 31 wherein at least one of the introducer, body, valve or elastomeric member is capable of being separated.

33. The medical apparatus of claim 31 further comprising a side port communicated with the hemostatic valve.

34. A combination of an introducer having a proximal hub including an inside surface, and a separable hemostatic valve, the hemostatic valve comprising:
 a separable body arranged and configured to be separable along a line of fissure or weakened seam into at least two portions having a distal portion; and
 a separable, fixed, compressible and torqueable elastomeric member arranged and configured to be separable along a line of fissure or weakened seam into at least two portions concentrically disposed around the distal portion of the separable body for providing a hemostatic seal between the inside surface of the hub and the separable body when the separable elastomeric member is disposed concentrically in and compressed within the hub by the separable body against the inside surface by means of the compression of the separable elastomeric member and the friction between the inside surface of the hub and the separable body with the separable elastomeric member, the separable elastomeric member being defined as torqueable due to a compression fit of the elastomeric member between the body of the hemostatic valve and tubular fitting of the introducer sufficient to provide a mechanically secure connection between the hemostatic valve body and tubular fitting, which mechanically secure connection allows torque to be securely transmitted to the introducer from hemostatic valve, the hemostatic seal and mechanically secure connection provided by the amount of the separable elastomer member confined between the body of the hemostatic valve and introducer and provided by the nature of the elastic composition of the separable elastomeric member.

35. The combination of claim 34 where the body is separable along a line of weakness and where the elastomeric member is at least partially cut through along a line aligned with the line of weakness of the body.

36. The combination of claim 34 where the body is separable along a line of weakness and where the elastomeric member is at provided in two separate portions having edges aligned with the line of weakness of the body.

37. The combination of claim 34 further comprising a side port communicated with the hemostatic valve.

* * * * *